US008167917B2

United States Patent
Chin et al.

(10) Patent No.: US 8,167,917 B2
(45) Date of Patent: May 1, 2012

(54) APPARATUS AND METHOD FOR SPINE FIXATION

(75) Inventors: Kingsley Richard Chin, Philadelphia, PA (US); Matthew Ibarra, Lakewood, CA (US)

(73) Assignee: Spinefrontier LLS, Philadelphia, PA (US)

( * ) Notice: Subject to any disclaimer, the term of this patent is extended or adjusted under 35 U.S.C. 154(b) by 1288 days.

(21) Appl. No.: 11/623,347

(22) Filed: Jan. 16, 2007

(65) Prior Publication Data

US 2007/0123869 A1 May 31, 2007

Related U.S. Application Data

(63) Continuation-in-part of application No. 10/669,927, filed on Sep. 24, 2003, now Pat. No. 7,282,064.

(60) Provisional application No. 60/759,446, filed on Jan. 17, 2006.

(51) Int. Cl.
*A61F 2/30* (2006.01)

(52) U.S. Cl. ...................................... 606/280

(58) Field of Classification Search .......... 606/246–279, 606/280–299, 70, 71; 623/17.11–17.16
See application file for complete search history.

(56) References Cited

U.S. PATENT DOCUMENTS

| | | | |
|---|---|---|---|
| 5,542,946 A * | 8/1996 | Logroscino et al. | 606/276 |
| 5,713,900 A * | 2/1998 | Benzel et al. | 606/250 |
| 6,146,382 A * | 11/2000 | Hurlbert | 606/286 |
| 6,547,790 B2 * | 4/2003 | Harkey et al. | 606/250 |
| 6,902,565 B2 * | 6/2005 | Berger et al. | 606/300 |
| 7,232,441 B2 * | 6/2007 | Altarac et al. | 606/250 |
| 7,608,106 B2 * | 10/2009 | Reiley | 623/17.11 |
| 7,618,443 B2 * | 11/2009 | Abdou | 606/278 |
| 7,621,942 B2 * | 11/2009 | Piehl | 606/281 |
| 7,695,500 B2 * | 4/2010 | Markworth | 606/280 |
| 2003/0163132 A1 * | 8/2003 | Chin | 606/61 |
| 2005/0240185 A1 * | 10/2005 | Boomer et al. | 606/69 |
| 2005/0273175 A1 * | 12/2005 | Gordon et al. | 623/17.16 |
| 2007/0118121 A1 * | 5/2007 | Purcell et al. | 606/61 |

OTHER PUBLICATIONS

Blackstone Medical Inc., Ascent Posterior Occipital Cervico-Thoracic System, http://www.blackstonemedical.com/ascent.php.
Medtronic Sofamor Danek USA, Inc., Vertex Reconstruction System, http://www.fda.gov/cdrh/pdf5/K053483.pdf.
Biomet, Altius M-INI Occipito-Cervico-Thoracic Spinal Fixation System, http://www.ebimedical.com/surgeons/trauma/index.cfm?pdid=0C&majcid=0B06&mincid=08&prodid=090303.

(Continued)

*Primary Examiner* — Thomas C. Barrett
*Assistant Examiner* — Christopher Beccia
(74) *Attorney, Agent, or Firm* — AKC Patents LLC; Aliki K. Collins

(57) ABSTRACT

A posterior spine fixation assembly includes a first elongated plate having first and second ends and a second elongated plate having first and second ends. The first and second elongated plates are arranged in an X-shaped configuration and are attached to each other via a first screw. The assembly also includes a first elongated rod having a first end configured to be removable attached to the second end of the first elongated plate and a second elongated rod having a first end configured to be removable attached to the second end of the second elongate plate. The assembly is attached to a first spine location with the first screw. The first and second plates are configured to rotate around an axis passing through the first screw and the distance between the first elongated rod and the second elongated rod is adjusted via this rotation.

15 Claims, 23 Drawing Sheets

OTHER PUBLICATIONS

Depuy Spine, Mountaineer Oct Spinal System, http://www.depuyspine.com/products/cervicaloct/mountaineer.asp.

Medtronic Sofamor Danek USA, Inc., CD Horizon Legacy Spinal System, http://www.sofamordanek.com/physician-spinal-spinal.html.

Global Orthopaedic Technology, Global Ortho—OctaFix (Cervical), http://www.globalortho.com.au/content/view/95/304/.

Stryker Spine, OASYS Occipito-Cervico-Thoracic Posterior System, http://www.stryker.com/spine/products_cervical_oasys.html.

* cited by examiner

APPARATUS AND METHOD FOR SPINE FIXATION

CROSS REFERENCE TO RELATED CO-PENDING APPLICATIONS

This application is a continuation in part of U.S. application Ser. No. 10/669,927 filed on Sep. 24, 2003 and entitled APPARATUS AND METHOD FOR CONNECTING SPINAL VERTEBRAE the contents of which are expressly incorporated herein by reference. This application also claims the benefit of U.S. provisional application Ser. No. 60/759,446 filed on Jan. 17, 2006 and entitled "APPARATUS AND METHOD FOR SPINE FIXATION", the contents of which are expressly incorporated herein by reference.

FIELD OF THE INVENTION

The present invention relates to an apparatus and a method for spine fixation, and more particularly to a spine fixation assembly having an adjustable width and utilizing a combination of plates and rods.

BACKGROUND OF THE INVENTION

The human spine comprises individual vertebras 30 (segments) that are connected to each other to form a spinal column 29, shown in FIG. 1. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems use rods 130, 140 that attach to screws 138, 136 inserted into the vertebral bodies, shown in FIG. 2. For spinal fixation in the cervical spine area 28, the proximal ends 151, 152 of the rods 130, 140, are molded to fit the anatomy of the skull 50 and the cervical spine 28 and are attached to an occipital fixation plate 150 that is implanted in the occiput 26.

Occipital fixation plates currently available are T-shaped, Y-shaped, or horseshoe-shaped, as shown in FIG. 2. All these types of occipital fixation plates have fixed geometrical shape and dimensions. In particular, the distance 135 between the lower ends of the plate is fixed, which requires that the rods 140, 130 are contoured during surgery so that they fit the anatomy of the patient. In general, most of the rod fixation systems require contouring of each rod across several vertebras in many cases. The contouring of each rod depends on the configuration of the screws and varies from side to side in the same patient and among patients. This contouring process may add considerable time to the surgery. Recent generations of screws and rod connectors seek to diminish this drawback by allowing variable axes of movements in the screw recess for the rod or in the rod connectors. However, in most cases this adds another level of complexity to the operation and often further increases the operative time. This increase in operative time and the complexity of the connectors put substantial stress on the surgeon and the supporting staff. Even in the hands of the best spine surgeon, the rod is often not perfectly contoured to align with the screws. Hence the surgeon has to use substantial force at multiple points along a rod to hold the rod to the screws or connectors while counteracting the adjacent soft tissues. This maneuver risks soft tissue damage and also puts the dura and the neural contents at risk for dural tears or spinal cord or nerve damage if a holding instrument slips.

A spine fixation assembly that utilizes plates instead of rods is described in U.S. Pat. No. 6,626,909, the contents of which are incorporated herein by reference. Referring to FIG. 3, a plate spine fixation assembly 600 connects adjacent vertebrae 92, 94 and 96. The spine fixation assembly 600 includes plates 610 and 612 which are placed diagonally to each other and transverse plates 614, 616. Plates 610 and 612 are attached to diagonally opposite pedicle screws and are cross-coupled at midpoint 608 forming an X-structure. The top and bottom pedicles 92A, 92B and 96A, 96B are connected with transverse plates 614 and 616, respectively. The basic X-shape structure may be repeated to extend the spine fixation in either caudad 672 or cephalad 670 directions. The modular structure of the spine fixation assembly 600 allows a surgeon to correct spinal deformities over any distance and orientation along the entire spine 29. However, for certain spinal locations, such as the occiput, rod or a combination of rods and plates may be preferred. Furthermore, there is a need for an occipital fixation assembly that has adjustable width and does not require contouring of elements during surgical implantation.

SUMMARY OF THE INVENTION

In general, in one aspect, the invention features a posterior spine fixation assembly including a first elongated plate having first and second ends and a second elongated plate having first and second ends. The first and second elongated plates are arranged in an X-shaped configuration and are attached to each other via a first screw. The assembly also includes a first elongated rod having a first end configured to be removable attached to the second end of the first elongated plate and a second elongated rod having a first end configured to be removable attached to the second end of the second elongate plate. The assembly is attached to a first spine location with the first screw.

Implementations of this aspect of the invention may include one or more of the following features. The distance between the first elongated rod and the second elongated rod is adjustable. The angle between the first and second elongated rods is adjustable. The first and second elongated plates are configured to rotate around an axis passing through the first screw and the distance between the first elongated rod and the second elongated rod is adjusted via this rotation. The first and second elongated plates comprise first through-bores for receiving the first screw. The first and second elongated plates further comprise second oval shaped through-bores, and a second screw is configured to pass through the oval shaped through-bores and to attach the first and second elongated plates to each other and to a second spine location after the distance between the first and second elongated rods has been adjusted. The oval shaped through-bores and the second screw form a sliding hinge that limits the range of the rotational motion of the elongated plates. The spine fixation assembly also includes first and second rod housings configured to be removable attached to the second ends of the first and second elongated plates, respectively, and the first ends of the first and second elongated rods are removable attached to the first and second housings, respectively. The second ends of the first and second elongated plates comprise third through-bores, adapted to receive the first and second rod housings, respectively. The first and second rod housings are configured to rotate around axes passing through the third through-bores and thereby to adjust the angle between the first and second elongated rods. The spine fixation assembly also includes first and second set screws used to removable attach the first and second elongated rods in the first and second rod housings, respectively. The first ends of the first and second elongated plates comprise fourth through-bores configured to receive third and fourth screws for attaching the assembly to third and fourth spine locations, respectively. The distance between the first elongated rod and the second elongated rod is adjusted in the range between 10 millimeters and 55 millimeters. The angle between the first elongated rod and the second elongated rod is adjusted in the range between 0 and 360 degrees. The first and second elongated plates are S-shaped. The first and second elongated plates have shapes that are rectangular, triangular, circular, oval, polygonal or combinations thereof. The first and second elongated plates are made of metal, plastic, ceramic, rubber, graphite, bone, absorbable material, composites, expandable materials under body temperature, glass, radiolucent materials or combinations thereof. The first spinal location is in the posterior occiput. Other spinal locations include other areas of the skull, pedicle, transverse processes, pars, lamina, vertebral body, sacrum, coccyx, lateral mass, spinous processes, or intervertebral discs The plates may be placed along the front, sides, or back of the spine through an anterior, lateral, oblique, posterior, or combined approach using an open, percutaneous, or minimally invasive approach under direct visualization, loupe or microscopic magnification, through a thoroscope, or navigational techniques with or without computer assistance. The first and second elongated plates may have adjustable lengths.

In general, in another aspect, the invention features a spine fixation method that includes providing a first elongated plate having first and second ends, providing a second elongated plate having first and second ends, arranging the first and second elongated plates in an X-shaped configuration and attaching them to each other via a first screw.

Next, attaching the X-shaped configuration to a first spine location with the first screw and then providing a first elongated rod and removable attaching a first end of the first elongated rod to the second end of the first elongated plate and finally providing a second elongated rod and removable attaching a first end of the second elongated rod to the second end of the second elongate plate.

In general, in another aspect, the invention features a spine fixation method that includes providing a first elongated plate having first and second end and attaching the first elongated plate's first end to a first spine location via a first screw. Next, providing a second elongated plate having first and second ends, and attaching the second elongated plate's first end to a second spine location via a second screw. Next, arranging the first and second elongated plates in an X-shaped configuration and attaching them to each other and to a third spine location with a third screw. Next, providing a first elongated rod and removable attaching a first end of the first elongated rod to the second end of the first elongated plate, and then providing a second elongated rod and removable attaching a first end of the second elongated rod to the second end of the second elongate plate.

In another embodiment, the plates may be preassembled attached in an X configuration with the crossing plates attached to each other by a screw, bolt, extensions off each plate that may be mated surface to surface or articulated and that allows rotation of the plates freely or incrementally and that may allow tightening at various angled positions. The crossing plates can be disassembled in or outside the patient or they may be fixed at a crossing point. In yet another embodiment, the plates could be configured in an H configuration. In yet another embodiment, the plates may each have one elongated hole that when overlapped allow one or more screws to be placed along the length of the holes instead of two individual holes along the center of each plate as shown in the current drawings. One plate could have one elongated hole and the other plate has two holes as shown in the current embodiment shown. Each plate may only have one hole each for screw placement versus the two holes shown in the drawings.

Among the advantages of this invention may be one or more of the following. The spine fixation assembly of this invention provides a rigid and compact structure with an adjustable width. This width flexibility allows the assembly to be adapted to various size spinal anatomies without requiring contouring of the stabilizing rods. Since rod contouring is not required, the time and complexity for the spinal fusion operation are reduced.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1:
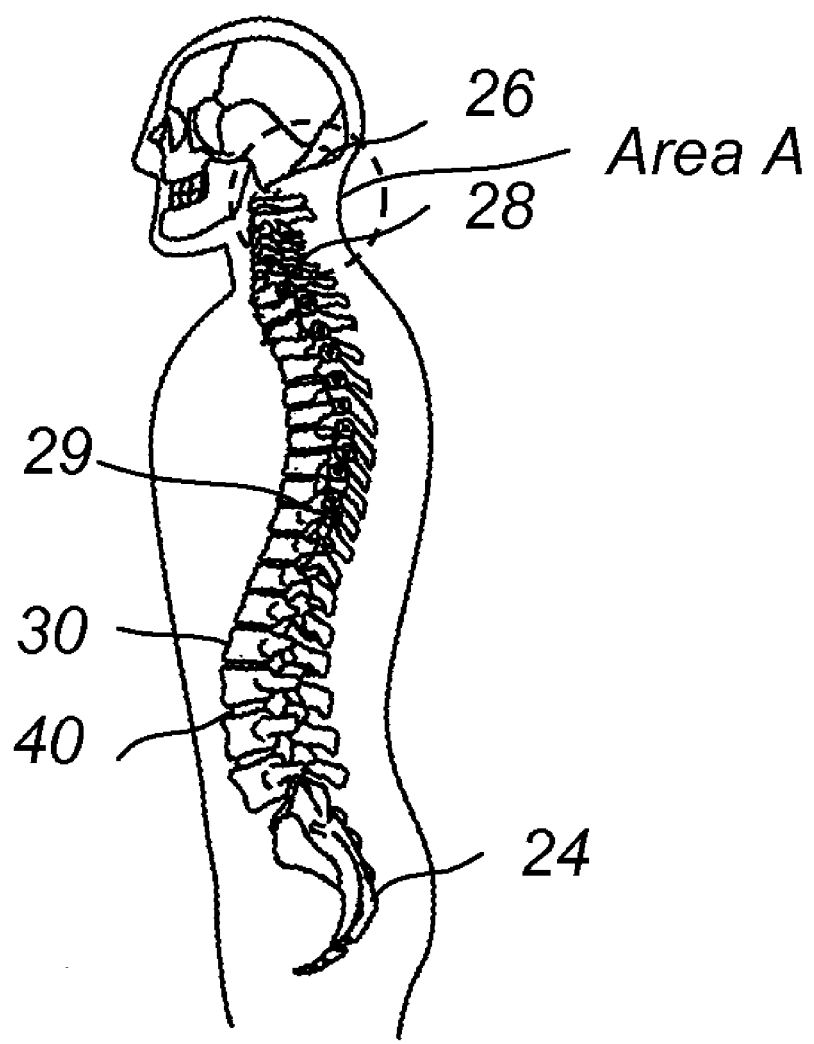
FIG. 1 is a side view of the human spinal column.
Figure 2:
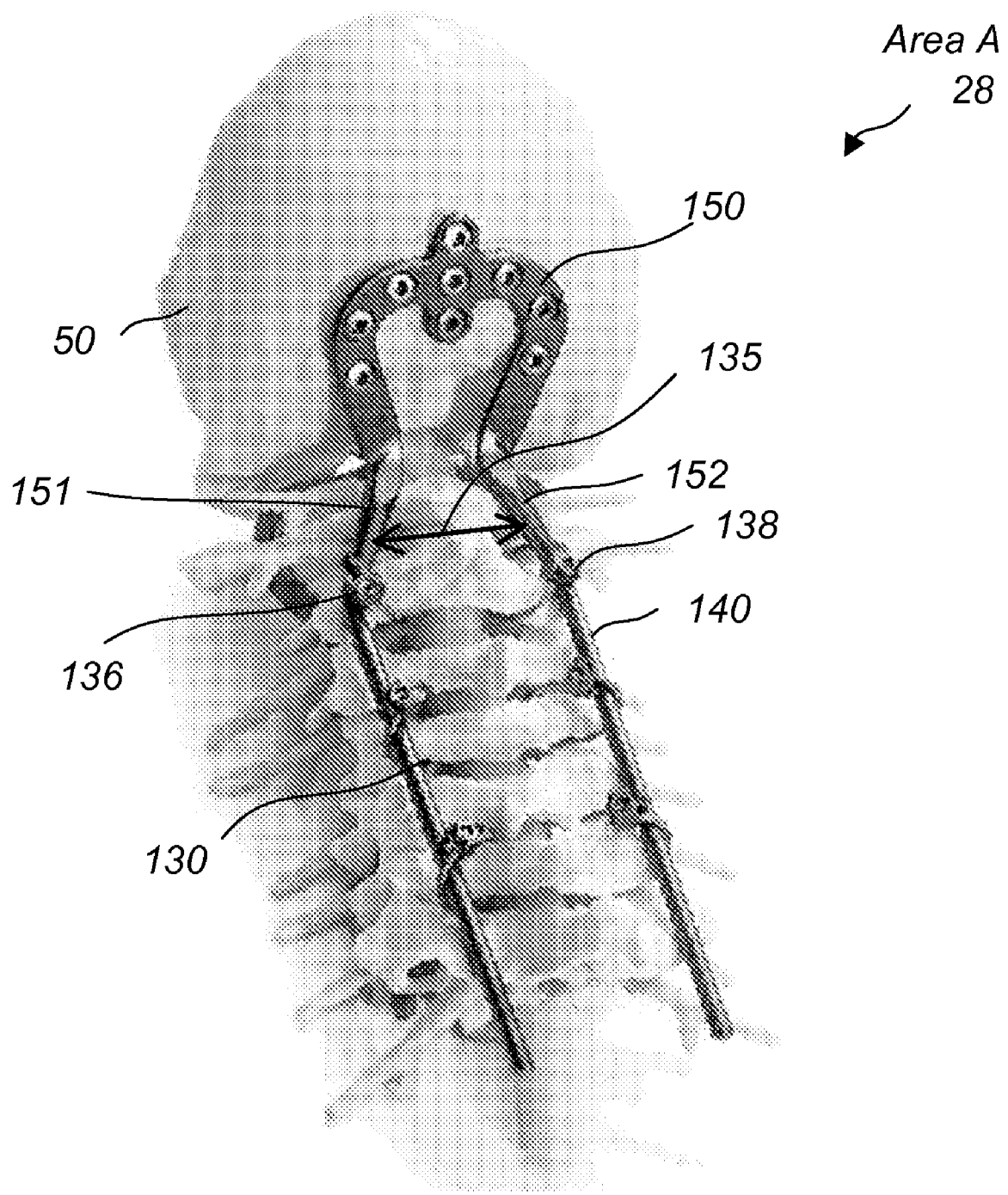
FIG. 2 is a prior art occipital cervical fixation system.
Figure 3:
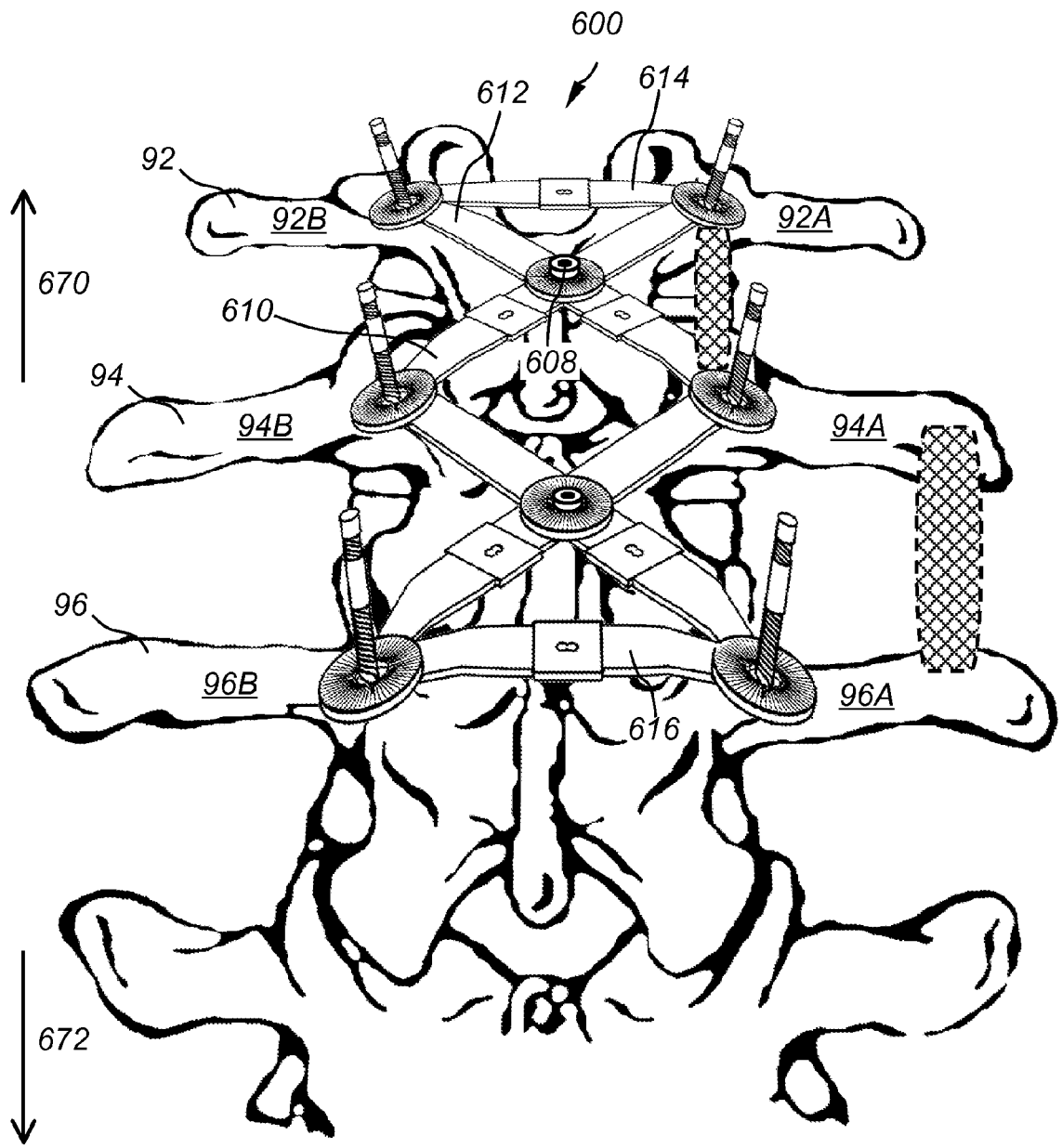
FIG. 3 is a prior art spine fixation system that utilizes plates forming an X-structure.
Figure 4:
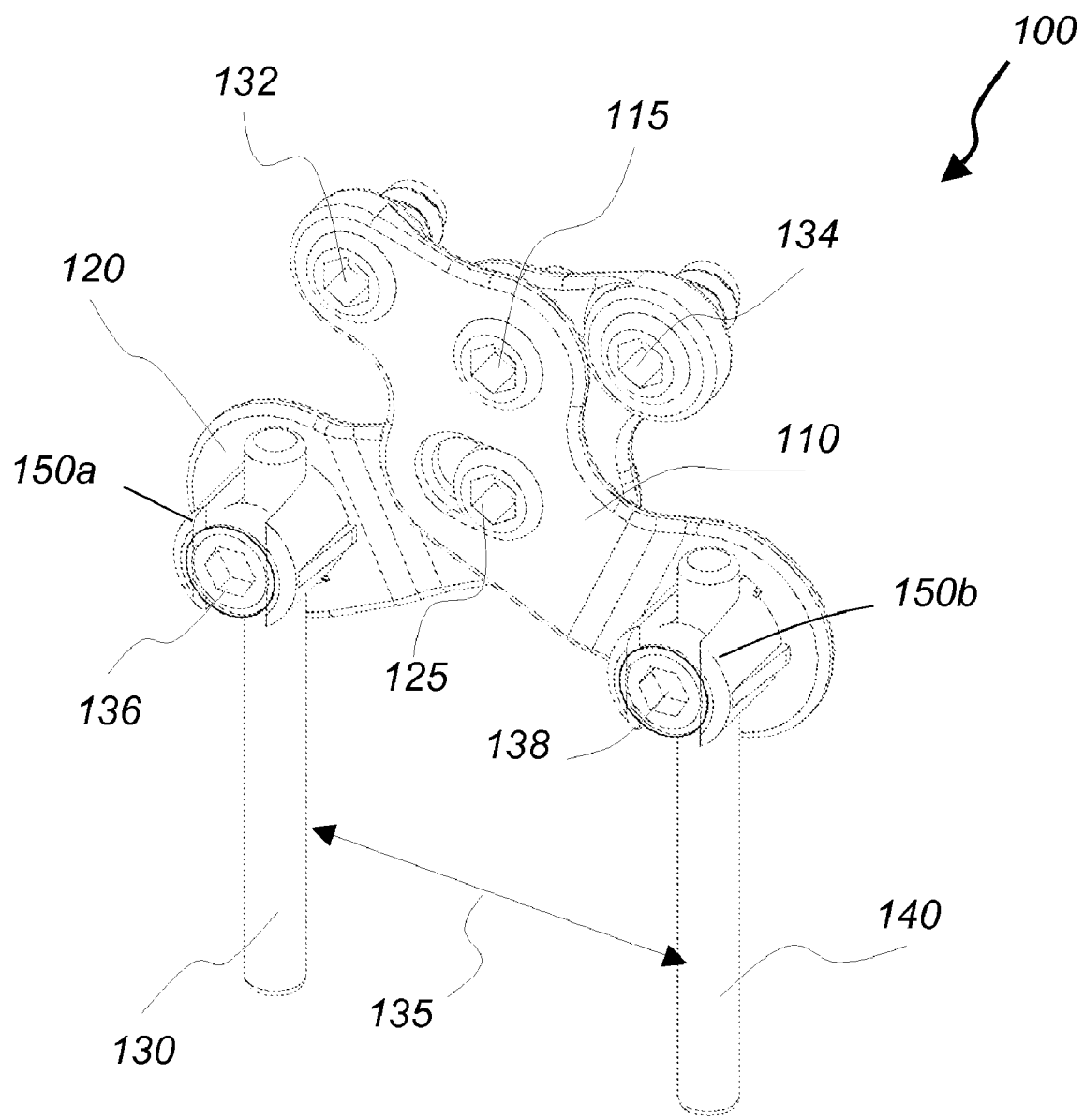
FIG. 4 is a perspective view of a first embodiment of the cervical spinal fixation assembly of this invention.
Figure 5:
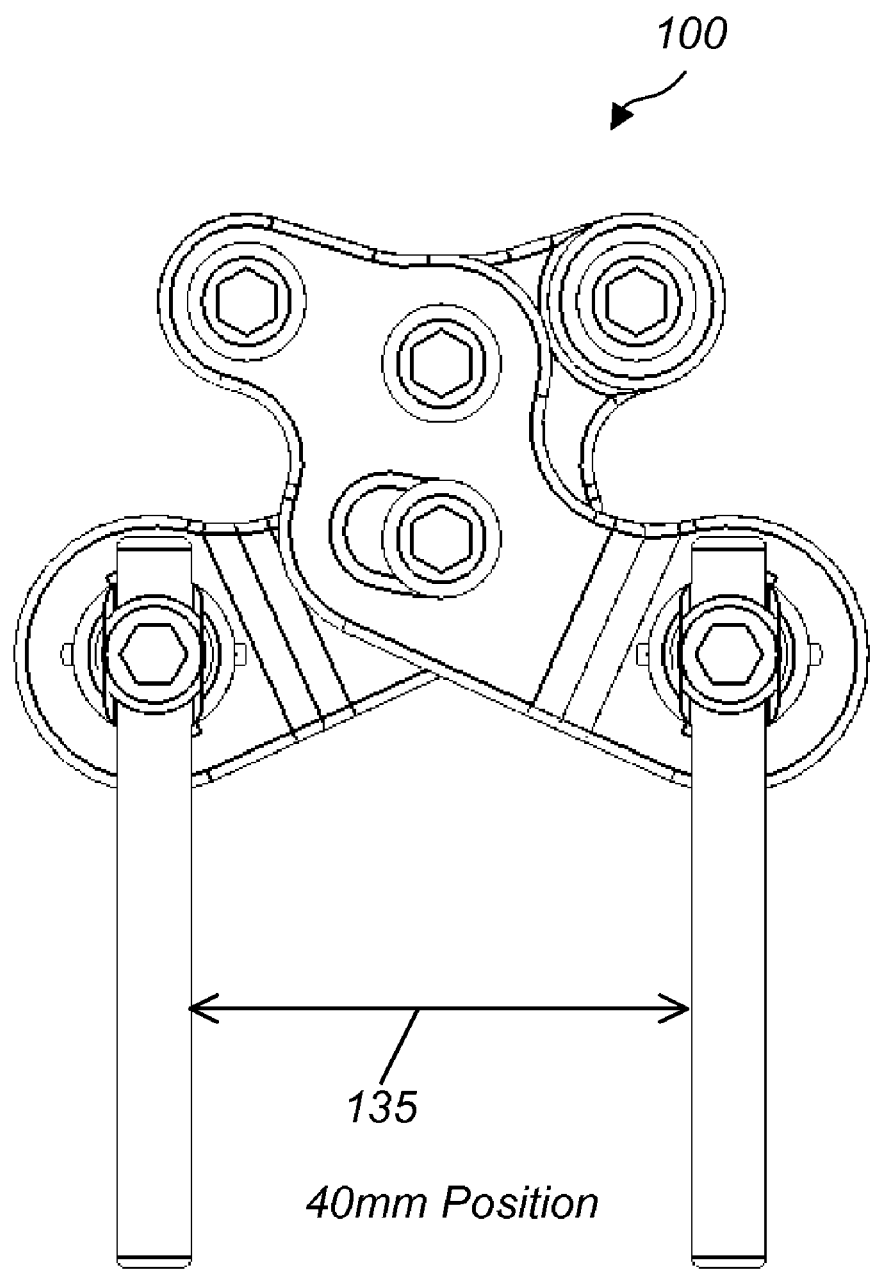
FIG. 5 is a front view of the cervical fixation assembly of FIG. 4.
Figure 6:
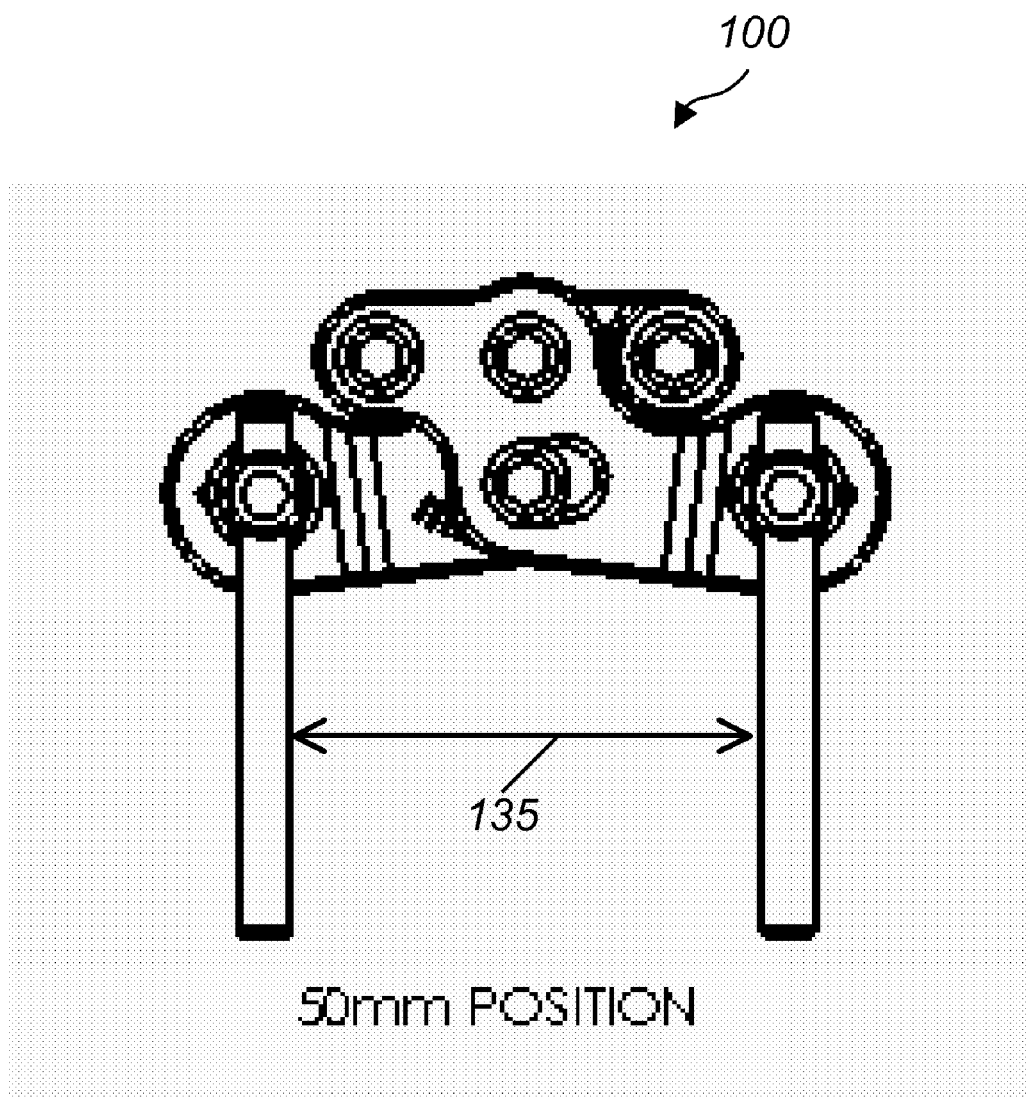
FIG. 6 is a front view of the cervical fixation assembly of FIG. 4 where the width of the device is increased.
Figure 7:
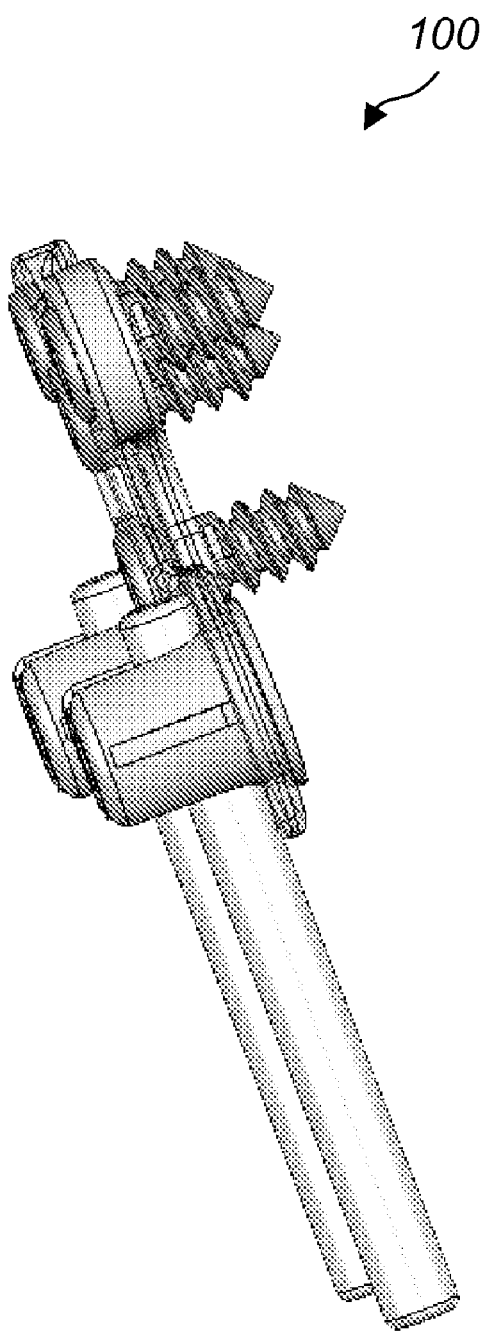
FIG. 7 is a side perspective view of the cervical fixation assembly of FIG. 4.
Figure 8:
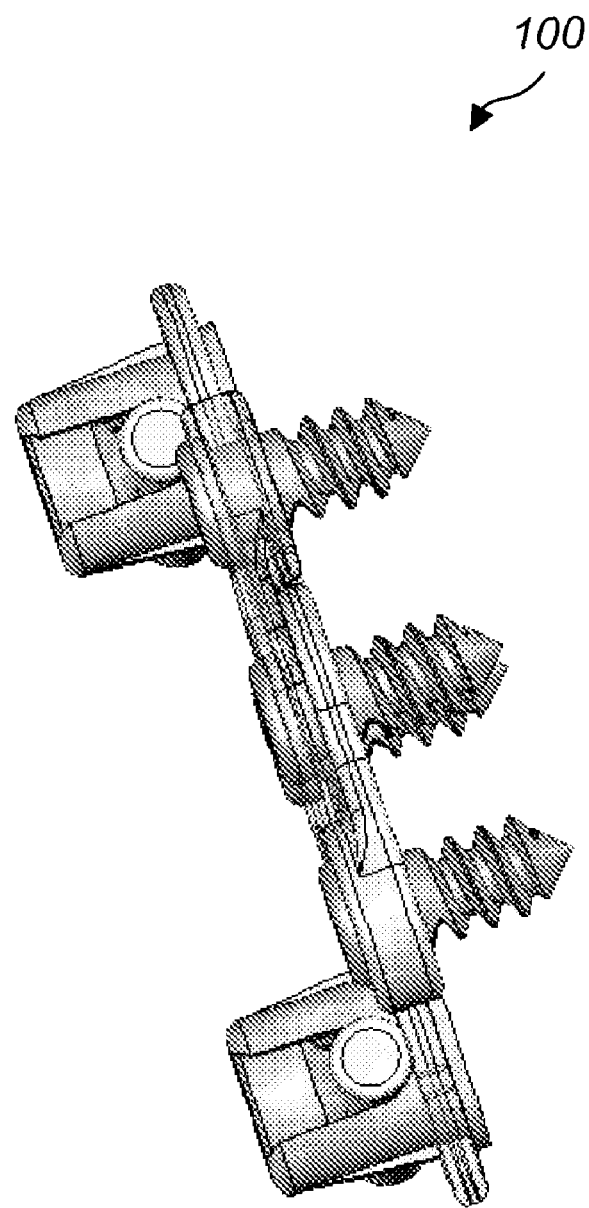
FIG. 8 is a top perspective view of the cervical fixation assembly of FIG. 4.
Figure 9:
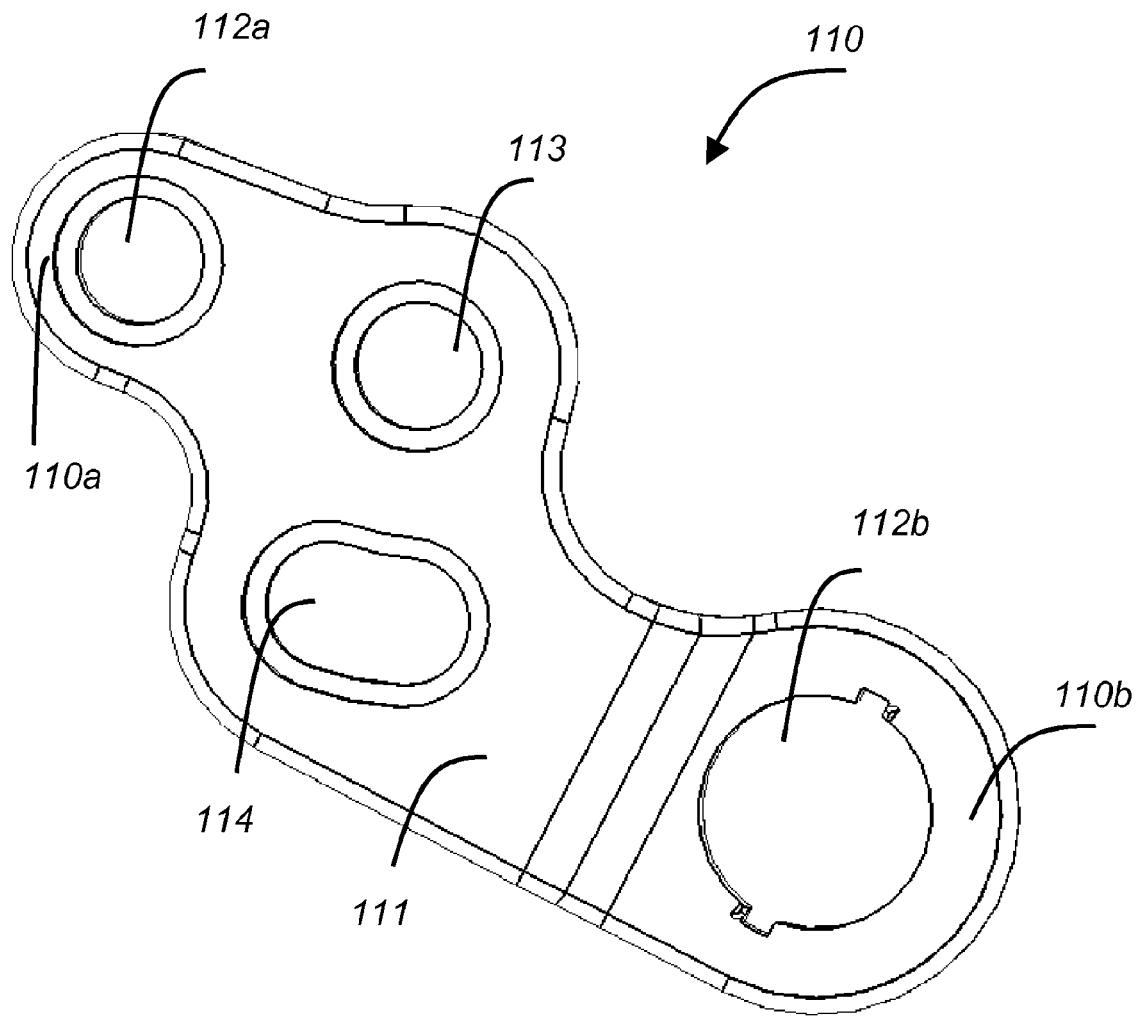
FIG. 9 is a front view of the front plate 110 of the cervical fixation assembly of FIG. 4.
Figure 10:
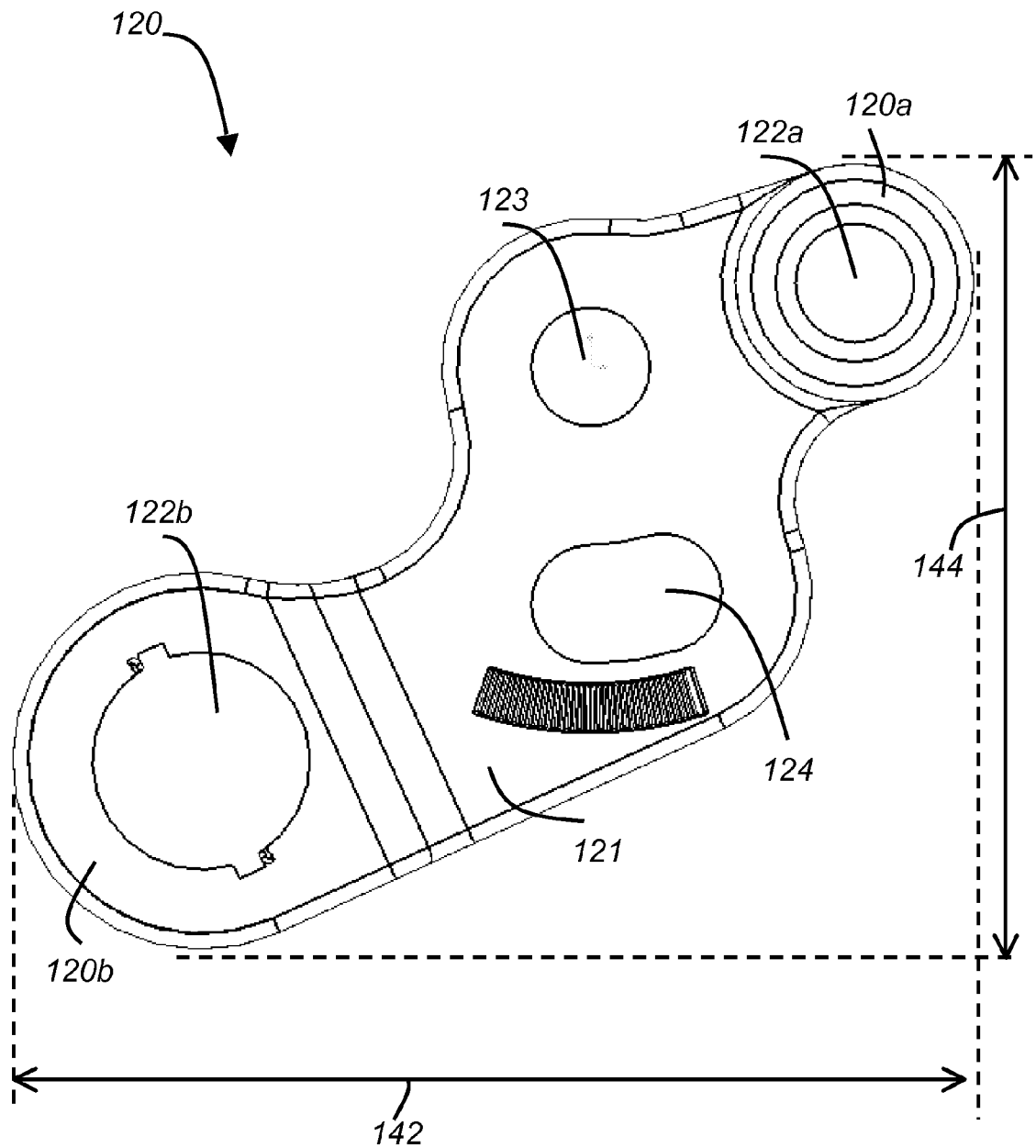
FIG. 10 is a front view of the back plate 120 of the cervical fixation assembly of FIG. 4.
Figure 11:
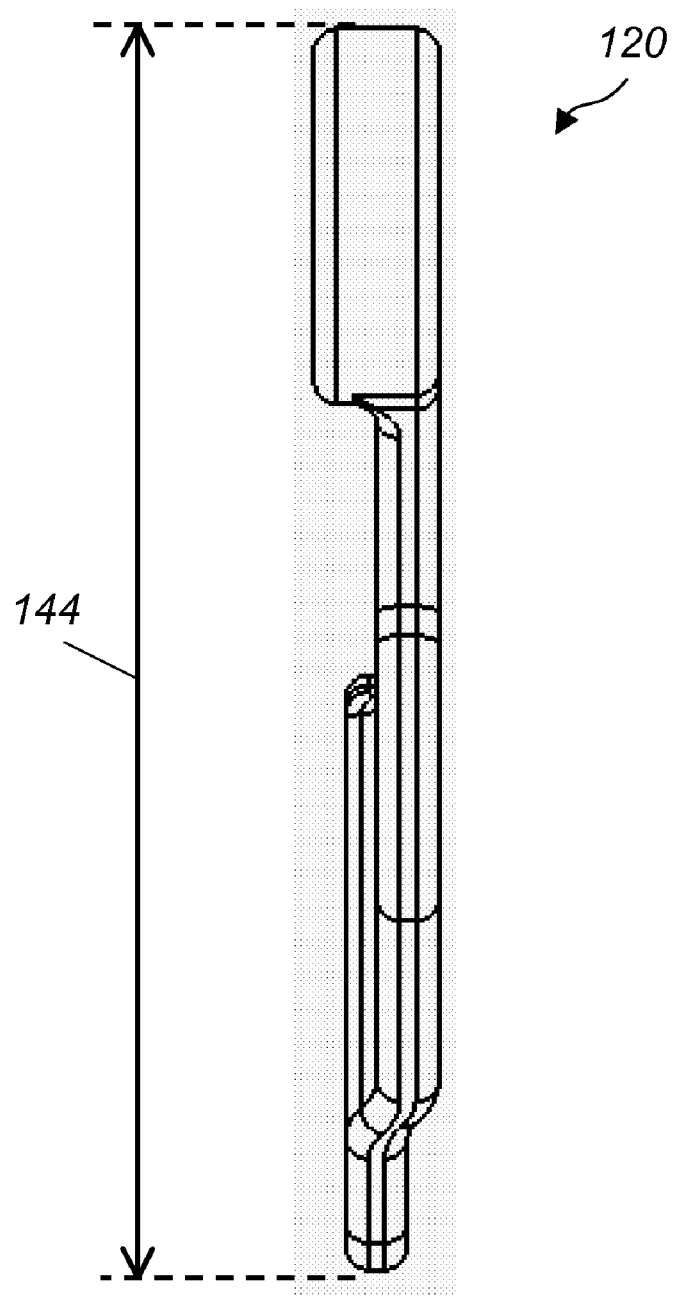
FIG. 11 is a side view of the back plate 120 of FIG. 11.
Figure 12:
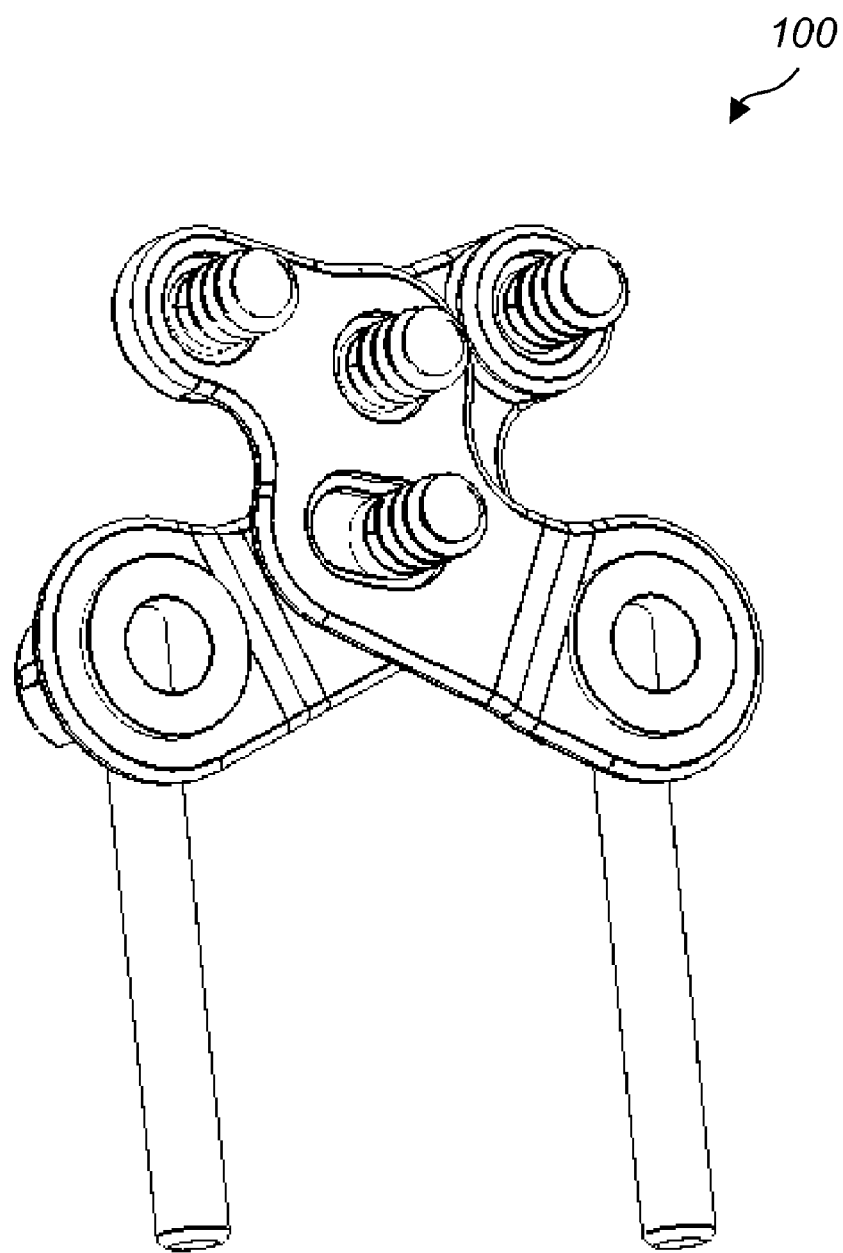
FIG. 12 is a back perspective view of the cervical fixation assembly of FIG. 4.
Figure 13:
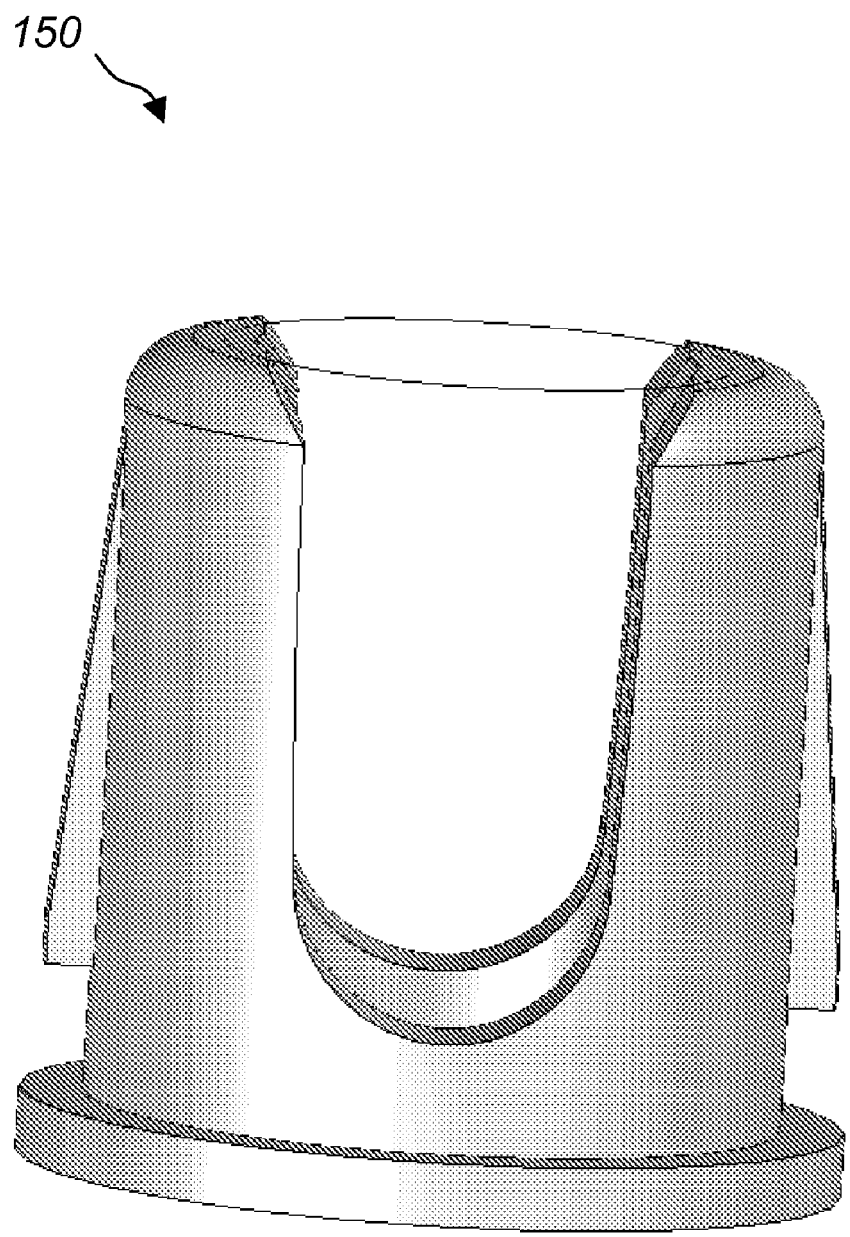
FIG. 13 is a side perspective view of the rod housing.

The present invention provides to a posterior cervical fixation system that utilizes a combination of rods and elongated plates arranged in an X-configuration. The spine fixation assembly includes a first s-shaped plate and a second s-shaped plate. The first and second plates are arranged in an X-configuration and are attached to each other and to the occiput via an upper central screw and a lower central screw. The upper central screw is threaded through circular shaped apertures of the first and second plates. The lower central screw is threaded through oval shaped apertures of the first and second plates. The oval shaped apertures allow the lower ends of the first and second plates to swing open or close. This action results in adjusting the distance between the lower ends of the first and second plates and thereby adjusting the width of the entire fixation assembly.

Referring to FIG. 4-FIG. 13, a posterior cervical fixation assembly 100 includes s-shaped elongated plates 110, 120 and rods 130, 140. Plates 110, 120 are arranged in an X-configuration and are attached to each other via central screws 115 and 125. Plates 110 and 120 have circular ends 110a, 110b and 120a, 120b and a wide midsection area 111 and 121, respectively, shown in FIG. 9 and FIG. 10, respectively. Ends 110a, 110b, 120a, 120b have apertures 112a, 112b, 122a and 122b, respectively. Each plate 110, 120 also includes central apertures 113, 114 and 123, 124, located in the midsection areas 111 and 121, respectively. Central apertures 113 and 123 have circular perimeters and central apertures 114 and 124 have oval perimeters. Plate 110 is a 180 degree mirror image of plate 120 and is placed on top of plate 120, so as to form the X-configuration. In this arrangement apertures 113 and 123 are aligned with each other and central screw 115 is threaded through them and attached to a first hole drilled in the occiput. Central oval apertures 114 and 124 are also aligned with each other and plates 110 and 120 are spread open and are adjusted to a desired distance 135 from each other. Central screw 125 is threaded through the aligned apertures 114, 124 and attached to a second hole drilled in the occiput. Central screws 115, 125 are tightened down to secure the position of the plates 110, 120 relative to each other at the set distance 135 and to the occiput. Additional screws 132, 134, are threaded through the upper apertures 110a, 120a of plates 110, 120, respectively, and are attached to additional holes drilled in the occiput, as well. Elongated rods 130 and 140 are attached to the lower apertures 122b and 112b of plates 120 and 110, respectively. Rods 130, 140 are placed within rod housing components 150a, 150b, respectively, and are secured with set screws 136 and 138, respectively. Rod housings 150a, 150b can rotate within apertures 122b, 112b, respectively, and in this way adjust the angle between rods 130 and 140 anywhere from 0 to 360 degrees. In one example, the distance 135 is in the range of 10 mm to 55 mm, the height 144 of the plates 110, 120 is in the range of 15 mm to 60 mm and the width 142 of the plates 110, 120 is in the range of 20 mm to 70 mm.

Figure 14A:
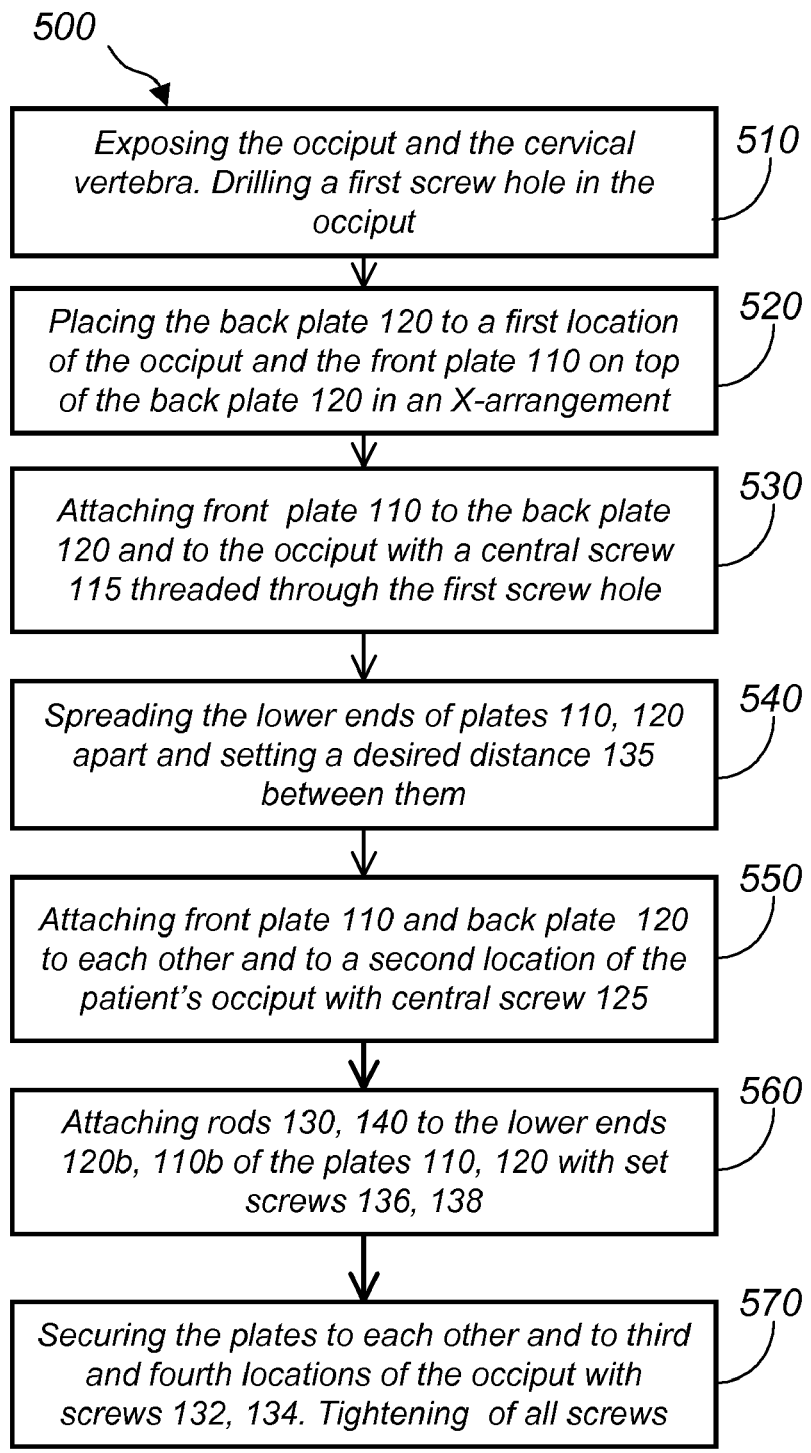
FIG. 14A is a block diagram of a cervical spinal fixation procedure according to one embodiment of this invention.

Referring to FIG. 14A, a method 500 of using the spine fixation assembly 100 comprises the following steps. Making an incision in the patient's pack exposing the occiput and the cervical vertebra. Drilling a first screw hole inside the occiput (510). Placing the back plate 120 to a first location of the occiput and placing the front plate 110 diagonally on top of the back plate 120 forming an X-configuration (520). Attaching the front plate and the back plate to each other and to the occiput with a central screw 115 threaded through the first screw hole (530). Spreading the lower ends of the front and back plates 110 and 120 apart and setting desired distance 135 between them (540). Attaching front and back plates 110 and 120 to each other and to the occiput with a second central screw 125 threaded through a second screw hole drilled below the first screw hole (550). Attaching rods 130, 140 to the lower ends 120b, 110b of the plates 110, 120, with set screws 136, 138, respectively and locking set screws (560). Drilling third and fourth holes in the occiput and attaching the front plate to the occiput with a screw 132 threaded through the third hole and the back plate to the occiput with a screw 134 threaded through the fourth hole, and finally tightening of all screws (570). In another embodiment, the second screw hole may be drilled before the first screw hole. First and second screw holes and central screws 115 and 125 may be in line vertically or oblique. Screws 136 and 138 may be in line horizontally or oblique. The distance between screws 136 and 138 in one embodiment may range from 10 mm to 40 mm. The distance between central screws 115 and 125 may range from 3 mm to 30 mm.

Figure 14B:
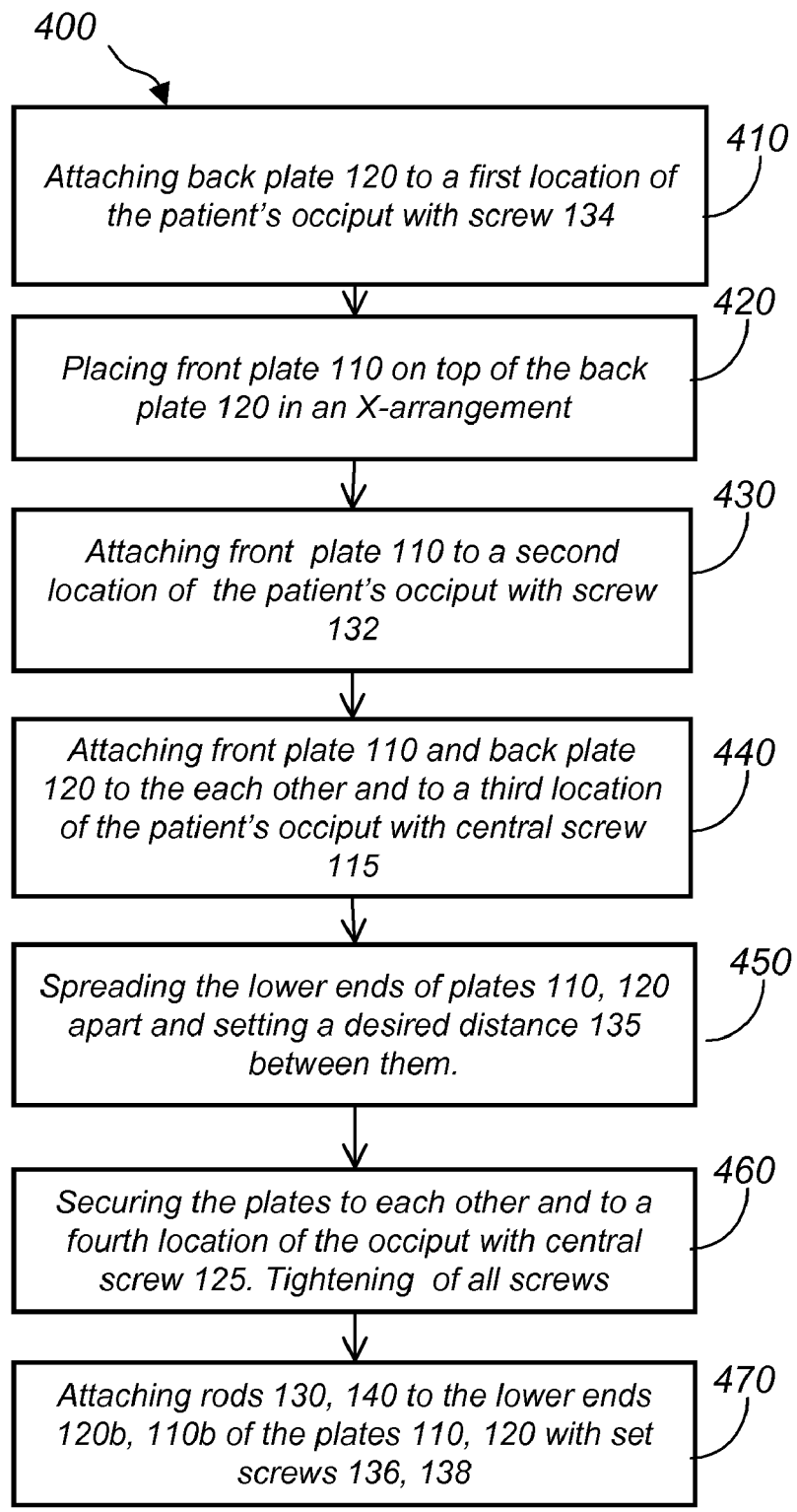
FIG. 14B is a block diagram of a cervical spinal fixation procedure according to another embodiment of this invention.
Figure 15A:
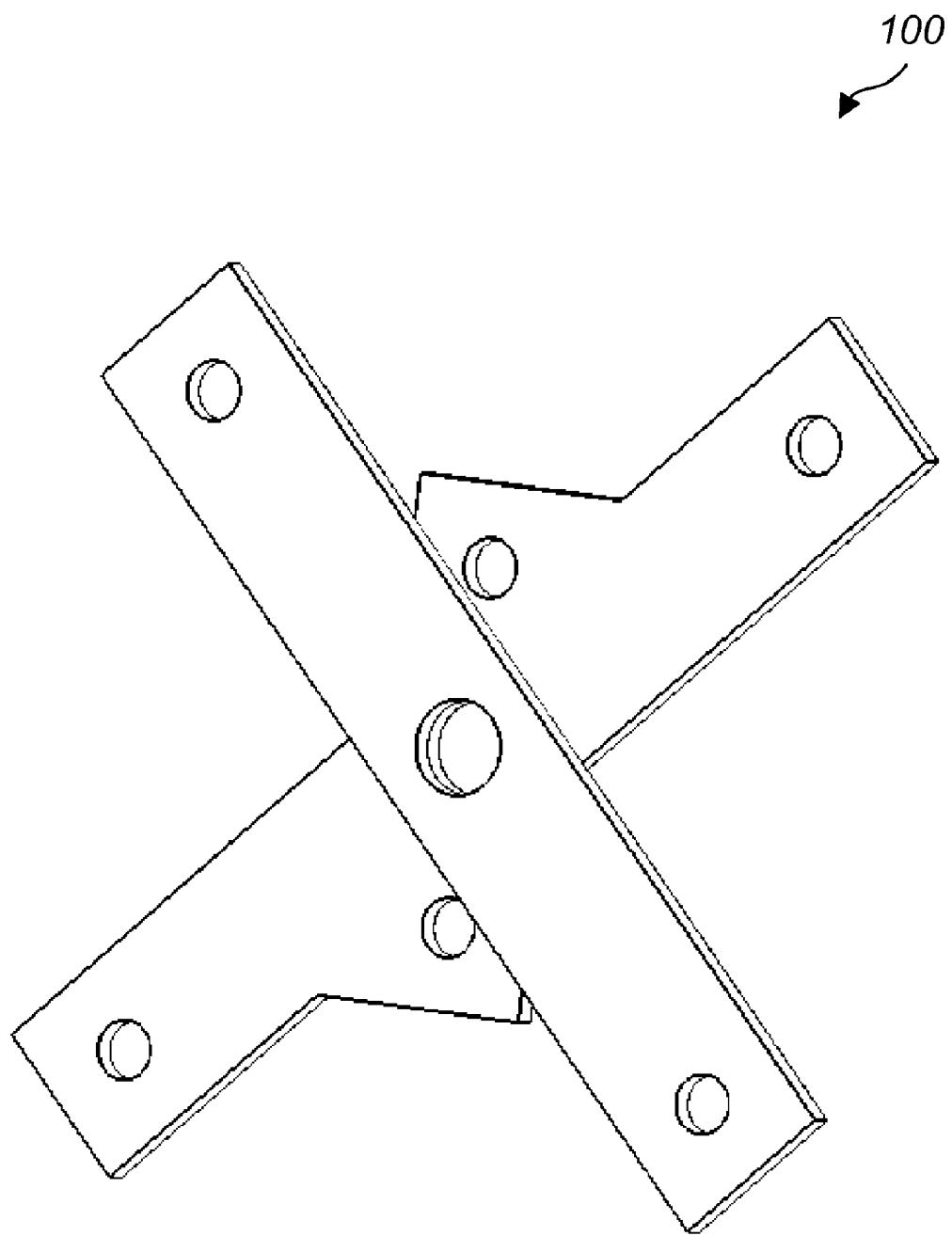
FIG. 15A-FIG. 15C is another embodiment of the spinal fixation assembly of this invention.
Figure 15B:
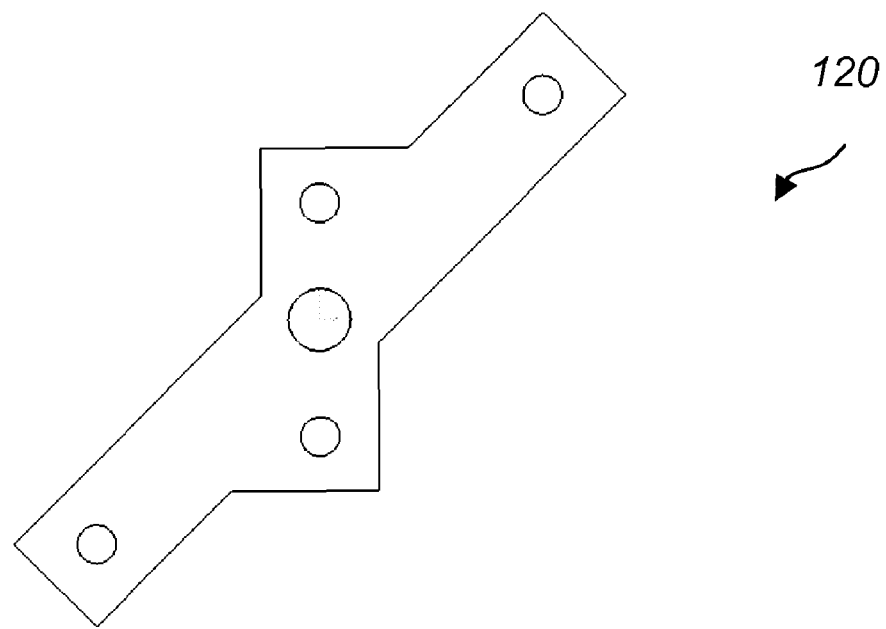
Figure 15C:
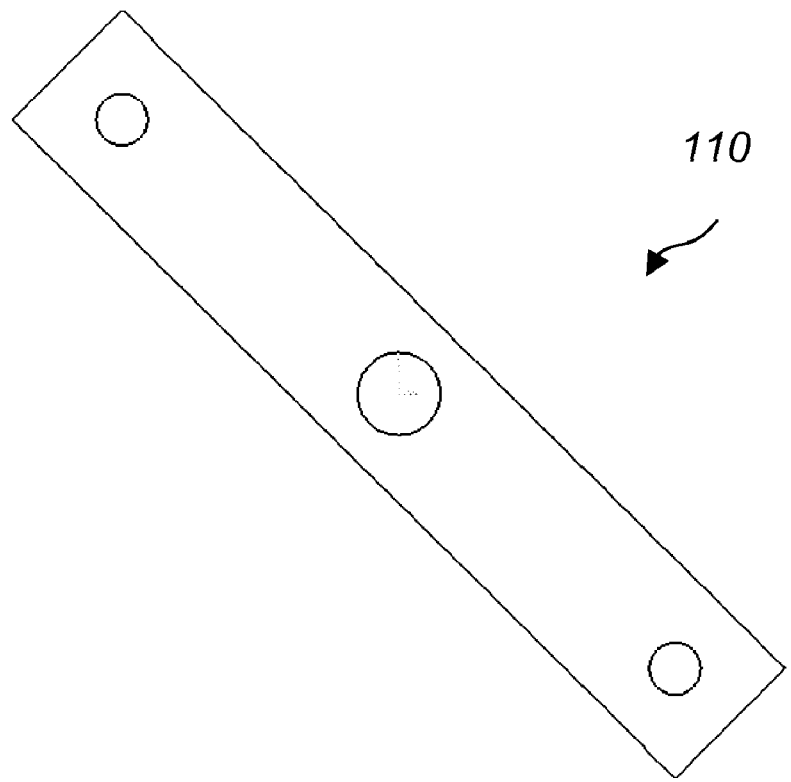
Figure 16A:
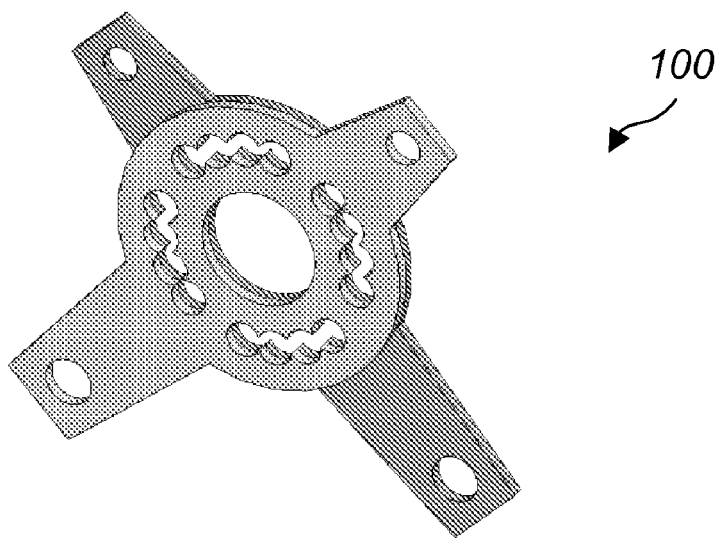
FIG. 16A-FIG. 16B is another embodiment of the spinal fixation assembly of this invention.
Figure 16B:
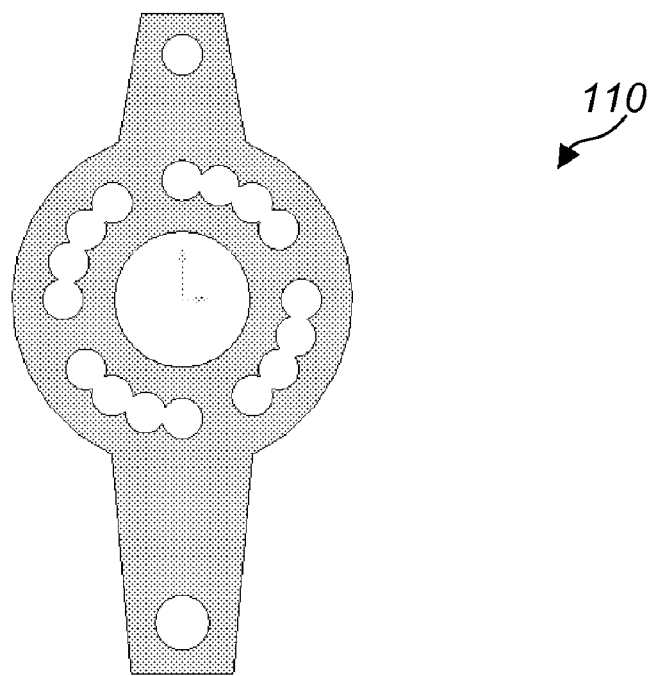
Figure 17A:
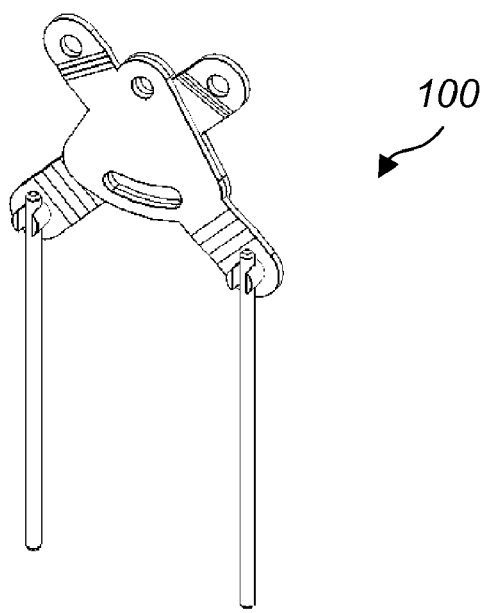
FIG. 17A-FIG. 17C is another embodiment of the spinal fixation assembly of this invention; and FIG. 18A
Figure 17B:
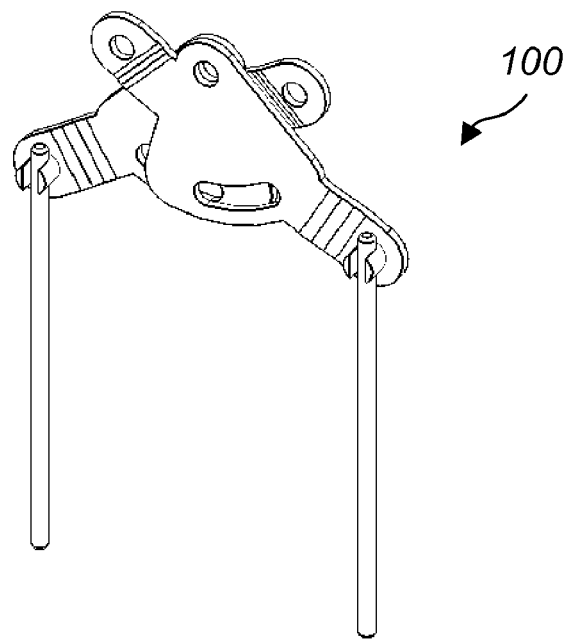
Figure 17C:
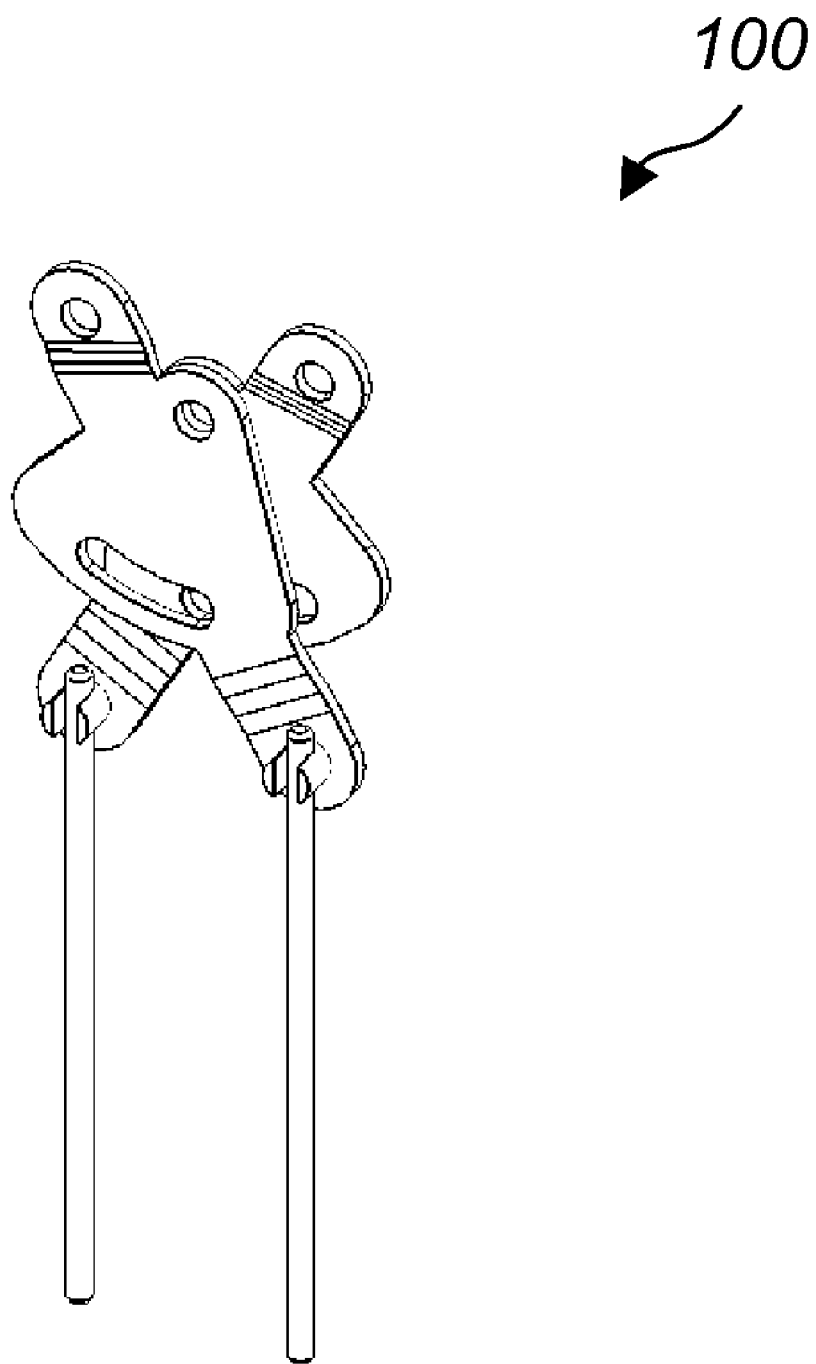
Figure 18A:
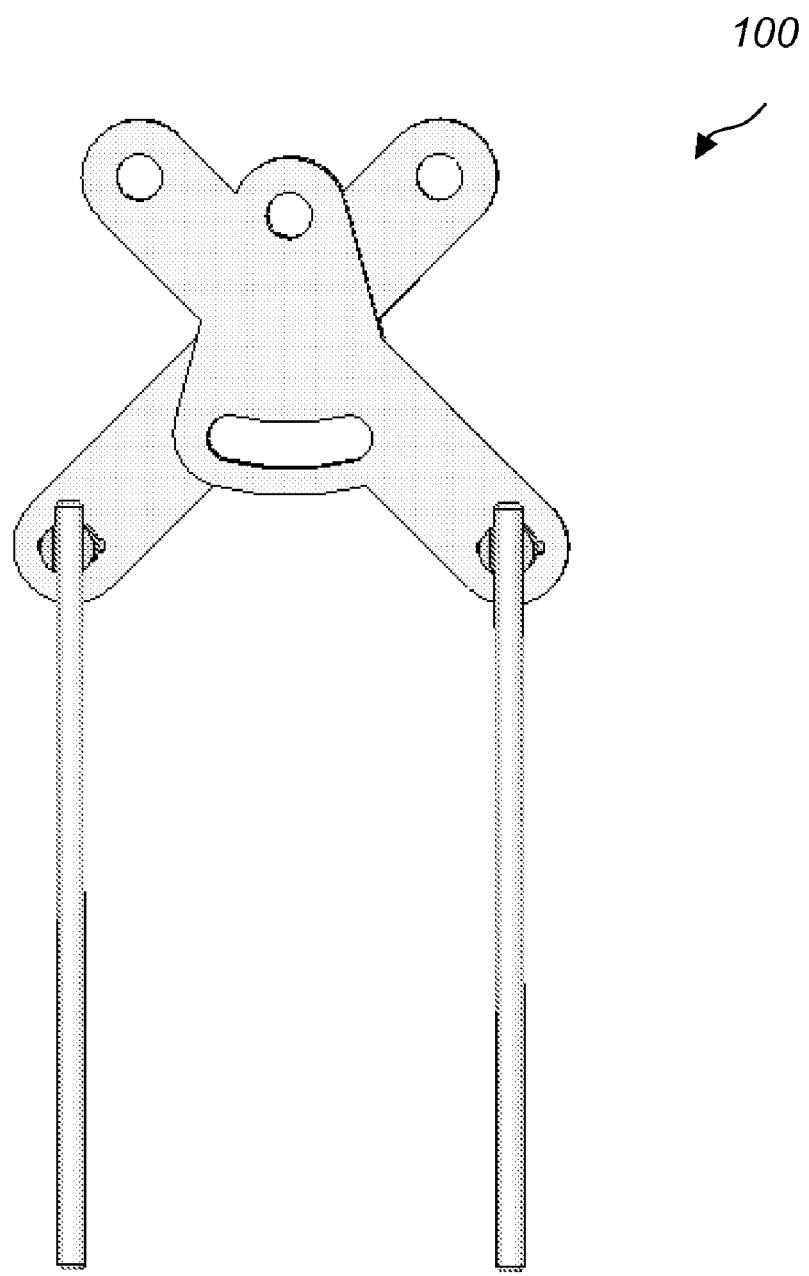
-FIG. 18E is another embodiment of the spinal fixation assembly of this invention.
Figure 18B:
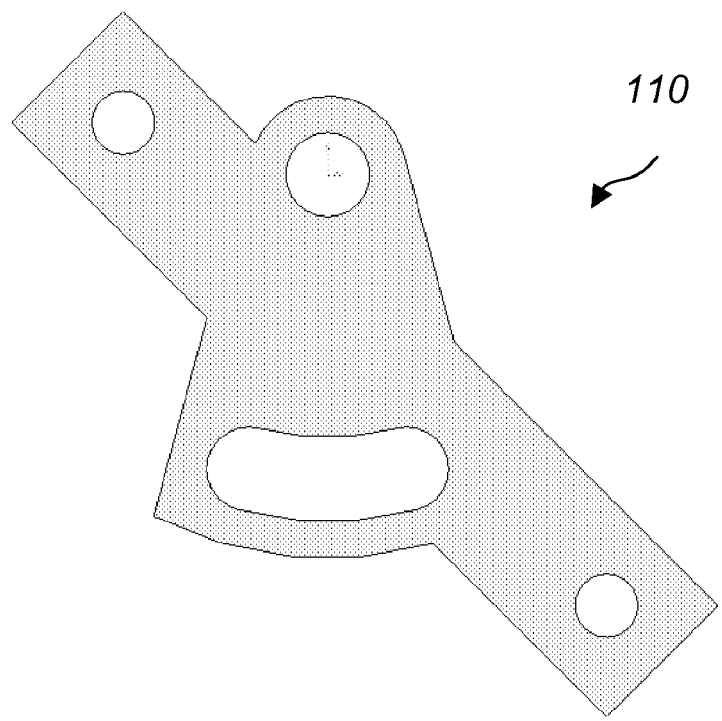
Figure 18C:
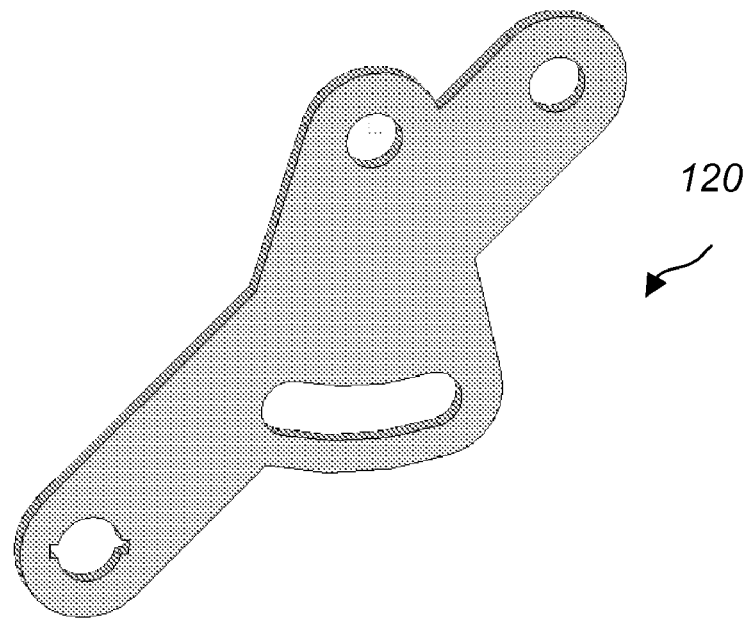
Figure 18D:
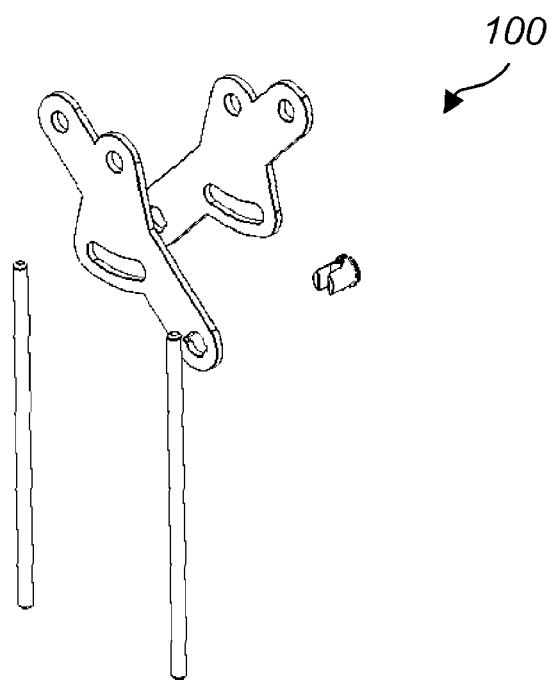
Figure 18E:
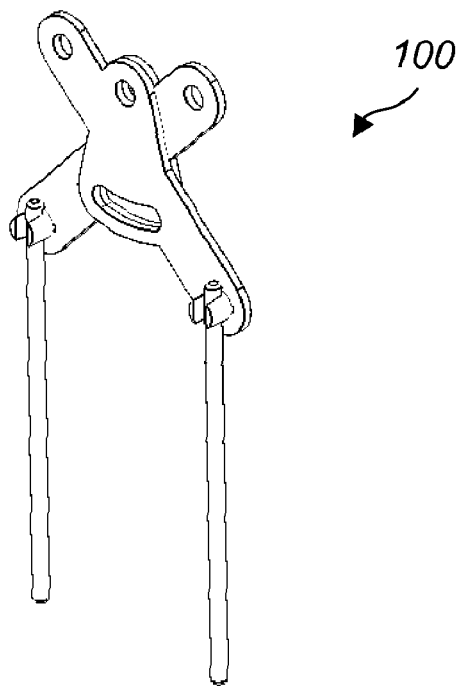

Referring to FIG. 14B, a method 400 of using the spine fixation assembly 100 comprises the following steps. Making an incision in the patient's back, exposing the occiput and the cervical spinal vertebrae and attaching the back plate 120 to a first location of the occiput with screw 134 threaded through a hole drilled in the first location of the occiput (410). Placing front plate 110 diagonally on top of the back plate 120 forming an X-configuration (420). Attaching front plate 110 to a second location of the patient's occiput with screw 132 threaded through a hole drilled in the second location of the occiput (430). Attaching front plate 110 and back plate 120 to each other and to a third location of the patient's occiput with central screw 115 threaded through a hole drilled in the third location of the occiput (440). Spreading the lower ends of front and back plates 110 and 120 apart and setting a desired distance 135 between them (450). Attaching front and back plates to each other and to a fourth location of the occiput with central screw 125 threaded through a hole drilled in the fourth location of the occiput (460). Attaching rods 130, 140 to the lower ends 120b, 110b of the plates 110, 120, with set screws 136, 138, respectively, and tightening of all screws.

In other embodiments of the spinal fixation assembly 100, plates 110, 120 may be rectangular, circular, triangular, any other polygonal shape, or any other combination thereof. Examples of these embodiments are shown in FIG. 15A-FIG.18E. The plates 110, 120 may be made of metal such as stainless steel, titanium, plastic, rubber, graphite, glass, expandable materials under body temperature, or other radiolucent materials. The plates may be placed along the front, sides, or back of the spine through an anterior, lateral, oblique, posterior, or combined approach using an open, percutaneous, or minimally invasive approach under direct visualization, loupe or microscopic magnification, through a thoroscope, or navigational techniques with or without computer assistance. In another embodiment, the plates may be preassembled attached in an X configuration with the crossing plates attached to each other by a screw, bolt, extensions off each plate that may be mated surface to surface or articulated and that allows rotation of the plates freely or incrementally and that may allow tightening at various angled positions. The crossing plates can be disassembled in or outside the patient or they may be fixed at a crossing point. In yet another embodiment, the plates could be configured in an H configuration.

In yet another embodiment, the plates may each have one elongated hole that when overlapped allow one or more screws to be placed along the length of the holes instead of two individual holes along the center of each plate as shown in the current drawings. One plate could have one elongated hole and the other plate may have two holes. Each plate may only have one hole each for screw placement versus the two holes shown in the drawings.

Several embodiments of the present invention have been described. Nevertheless, it will be understood that various modifications may be made without departing from the spirit and scope of the invention. Accordingly, other embodiments are within the scope of the following claims.

What is claimed is:

1. A posterior spine fixation assembly comprising:
a first elongated plate having first and second ends;
a second elongated plate having first and second ends, wherein the first and second elongated plates are arranged in an X-shaped configuration and are attached to each other via a first screw, and wherein the first and second elongated plates comprise first through-bores for receiving the first screw;
a first elongated rod having a first end configured to be removable attached to the second end of the first elongated plate;
a second elongated rod having a first end configured to be removable attached to the second end of the second elongate plate;
wherein said first and second elongated rods extend along a direction in the plane of the X-shaped configuration;
wherein the assembly is attached to a first spine location with the first screw;
wherein the distance between the first and second elongated rods is adjusted by rotating said first elongated plate relative to said second elongated plate around an axis passing through the first screw;
wherein the first and second elongated plates further comprise second oval shaped through-bores and a second screw is configured to pass through the oval shaped through-bores and to attach the first and second elongated plates to each other and to a second spine location after the distance between the first and second elongated rods has been adjusted; and
wherein the oval shaped through-bores and the second screw form a sliding hinge that limits the range of the rotational motion of the elongated plates.

2. The spine fixation assembly of claim 1 wherein the angle between the first and second elongated rods is adjustable.

3. The spine fixation assembly of claim 1 further comprising first and second rod housings configured to be removable attached to the second ends of the first and second elongated plates, respectively, and wherein the first ends of the first and second elongated rods are removable attached to the first and second housings, respectively.

4. The spine fixation assembly of claim 3 wherein the second ends of the first and second elongated plates comprise third through-bores adapted to receive the first and second rod housings, respectively.

5. The spine fixation assembly of claim 4 wherein the first and second rod housings are configured to rotate around axes passing through the third through-bores and thereby to adjust the angle between the first and second elongated rods.

6. The spine fixation assembly of claim 5 further comprising first and second set screws used to removable attach the first and second elongated rods in the first and second rod housings, respectively.

7. The spine fixation assembly of claim 1 wherein the first ends of the first and second elongated plates comprise fourth through-bores configured to receive third and fourth screws for attaching the assembly to third and fourth spine locations, respectively.

8. The spine fixation assembly of claim 1 wherein the distance between the first elongated rod and the second elongated rod is adjusted in the range between 10 millimeters and 55 millimeters.

9. The spine fixation assembly of claim 3 wherein the angle between the first elongated rod and the second elongated rod is adjusted in the range between 0 and 360 degrees.

10. The spine fixation assembly of claim 1 wherein the first and second elongated plates are S-shaped.

11. The spine fixation assembly of claim 1 wherein the first and second elongated plates have shapes comprising one of rectangular, triangular, circular, oval, polygonal -or combinations thereof.

12. The spine fixation assembly of claim 1 wherein the first and second elongated plates comprise materials selected from a group consisting of metal, plastic, ceramic, rubber, graphite, bone, absorbable material, composites, expandable materials under body temperature, glass, radiolucent materials and combinations thereof.

13. The spine fixation assembly of claim 1 wherein the first spinal location is in the posterior occiput.

14. The spine fixation assembly of claim 8 wherein the spinal locations comprise one of occiput, other areas of the skull, pedicle, transverse processes, pars, lamina, vertebral body, sacrum, coccyx, lateral mass, spinous processes, or intervertebral discs.

15. The spine fixation assembly of claim 1 wherein the first and second elongated plates comprise adjustable lengths.

* * * * *